US011576898B2

(12) United States Patent
Lim et al.

(10) Patent No.: US 11,576,898 B2
(45) Date of Patent: Feb. 14, 2023

(54) PREPARATION CONTAINING BENZIMIDAZOLE DERIVATIVE

(71) Applicant: HK INNO.N CORPORATION, Seoul (KR)

(72) Inventors: Hyungsuk Lim, Gyeonggi-do (KR); Chun Seon Lyu, Gyeonggi-do (KR); Sun Young Park, Gyeonggi-do (KR); Kyungmin Shin, Seoul (KR); Da Won Oh, Gyeonggi-do (KR)

(73) Assignee: HK INNO.N CORPORATION, Chungcheongbuk-do (KR)

( * ) Notice: Subject to any disclaimer, the term of this patent is extended or adjusted under 35 U.S.C. 154(b) by 231 days.

(21) Appl. No.: 16/473,748

(22) PCT Filed: Dec. 26, 2017

(86) PCT No.: PCT/KR2017/015489
§ 371 (c)(1),
(2) Date: Jun. 26, 2019

(87) PCT Pub. No.: WO2018/124700
PCT Pub. Date: Jul. 5, 2018

(65) Prior Publication Data
US 2020/0392120 A1 Dec. 17, 2020

(30) Foreign Application Priority Data
Dec. 26, 2016 (KR) ........................ 10-2016-0179334

(51) Int. Cl.
*A61K 31/4184* (2006.01)
*A61K 9/00* (2006.01)
*A61K 9/20* (2006.01)

(52) U.S. Cl.
CPC ........ *A61K 31/4184* (2013.01); *A61K 9/0053* (2013.01); *A61K 9/2027* (2013.01); *A61K 9/2054* (2013.01); *A61K 9/2059* (2013.01); *A61K 9/2063* (2013.01); *A61K 9/2072* (2013.01); *A61K 9/2009* (2013.01)

(58) Field of Classification Search
CPC .............. A61K 31/4184; A61K 9/0053; A61K 9/2054
See application file for complete search history.

(56) References Cited

U.S. PATENT DOCUMENTS

| 7,723,321 | B2 | 5/2010 | Hanazawa et al. |
| 9,034,860 | B2 | 5/2015 | Watanabe et al. |
| 2007/0142448 | A1 | 6/2007 | Hanazawa et al. |
| 2010/0093786 | A1 | 4/2010 | Watanabe et al. |
| 2018/0338954 | A1 | 11/2018 | Lee et al. |
| 2020/0069652 | A1 | 3/2020 | Lee et al. |

FOREIGN PATENT DOCUMENTS

| JP | 2009-520017 | 5/2009 |
| KR | 10-2008-0080195 | 9/2008 |
| KR | 10-1506043 | 3/2015 |
| TW | 200732326 | 9/2007 |
| WO | 2007/072146 | 6/2007 |
| WO | 2007/138606 | 12/2007 |
| WO | 2016/200148 | 12/2016 |

OTHER PUBLICATIONS

Extended European Search Report, dated Jul. 20, 2020 in corresponding European Patent Application No. 17888189.2.
Manivaiman et al., "Formulation development and evaluation of Naproxen sodium tablets USP", International Journal of Drug Development & Research, 2010, vol. 2, No. 1, pp. 47-53.
Patel et al., "Formulation and evaluation of once a day regioselective dual component tablet of atorvastatin calcium and metoprolol succinate", International Journal of PharmTech Research, 2010, vol. 2, No. 3, pp. 1870-1882.
Notification of Reasons for Rejection dated May 12, 2020 in corresponding Japanese Patent Application No. 2019-533412, with English Translation.
English translations of International Preliminary Report on Patentability and Written Opinion dated Jul. 2, 2019 in International (PCT) Application No. PCT/KR2017/015489.
International Search Report dated Apr. 23, 2018 in International Application No. PCT/KR2017/015489.
Kawashima, Y. et al., "Low-substituted Hydroxypropylcellulose as a Sustained-Drug Release Matrix Base or Disintegrant Depending on Its Particle Size and Loading in Formulation", Pharmaceutical Research, 1993, vol. 10, No. 3, pp. 351-355. See abstract; and pp. 352-354.
Rahman, M. et al., "Effect of Mode of Addiction of Disintegrants on Dissolution of Model Drug From Wet Granulation Tablets", International Journal of Pharma Sciences and Research, 2011, vol. 2, No. 2, pp. 84-92.
Mohanachandran, P.S et al., "Superdisintegrants: An Over View", International Journal of Pharmaceutical Sciences Review and Research, Jan.-Feb. 2011, vol. 6, No. 1, article-022, inner pp. 105-109.

*Primary Examiner* — Alicia L Otton
(74) *Attorney, Agent, or Firm* — Giordano Law LLC; David A. Giordano

(57) ABSTRACT

The present invention relates to a novel formulation comprising a benzimidazole derivative. The formulation for oral administration comprising a compound of Formula 1 according to the present invention or a pharmaceutically acceptable salt thereof; and at least one disintegrant selected from the group consisting of croscarmellose sodium, sodium starch glycolate and low-substituted hydroxypropylcellulose, exhibits an excellent storage stability and has an effect on preventing a phenomenon of decline in dissolution rate, thus being usefully used as a formulation for oral administration.

7 Claims, 4 Drawing Sheets

[Figure 1]
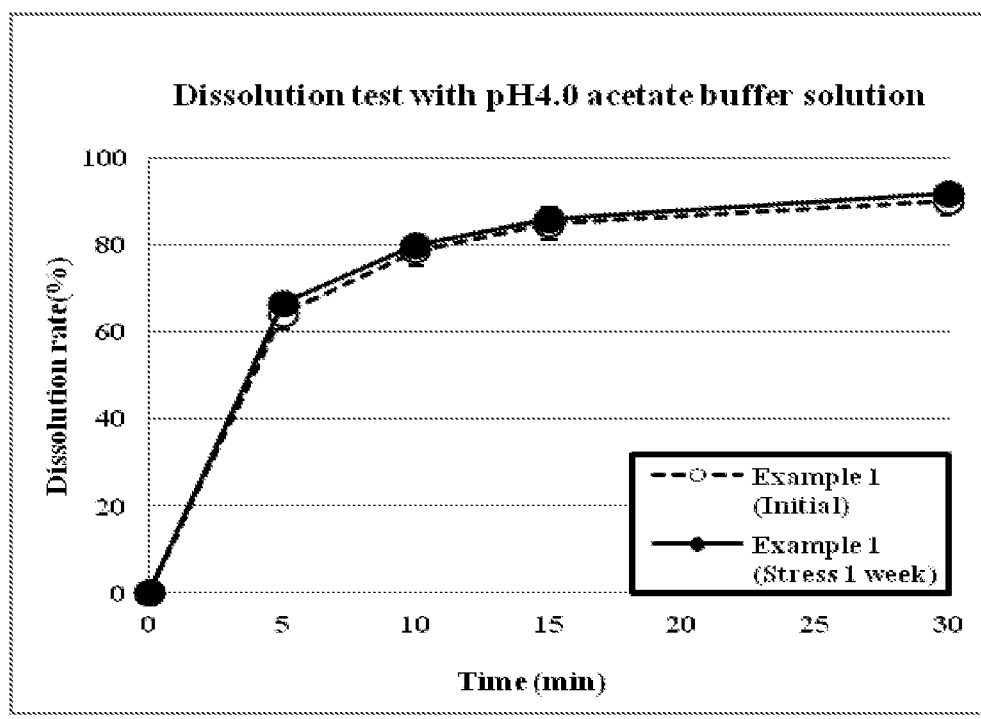

【Figure 2】
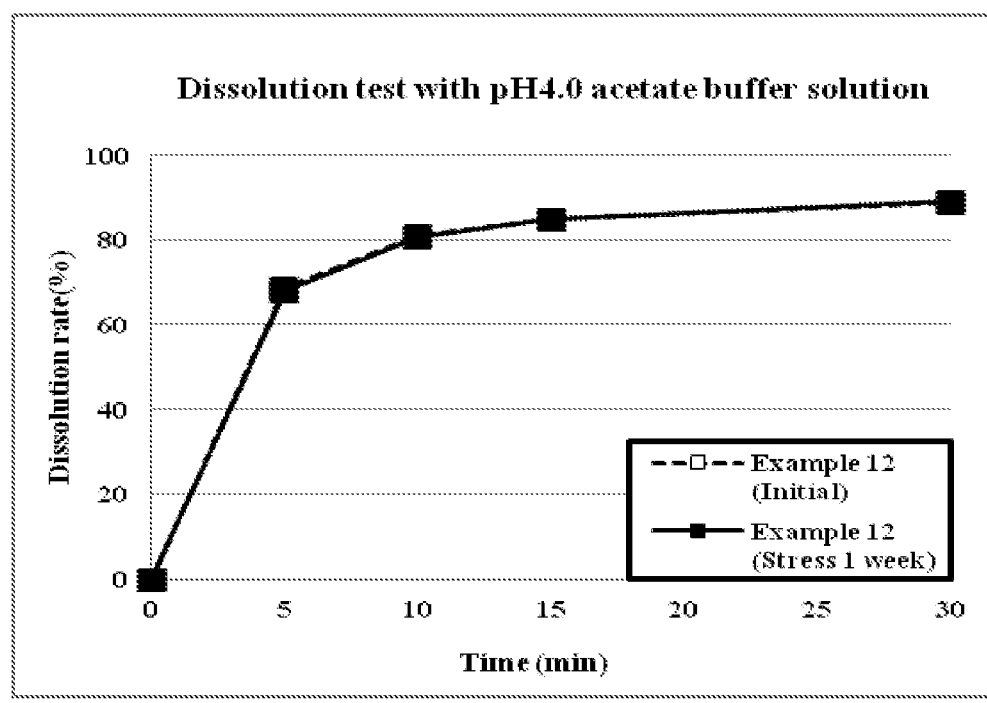

【Figure 3】
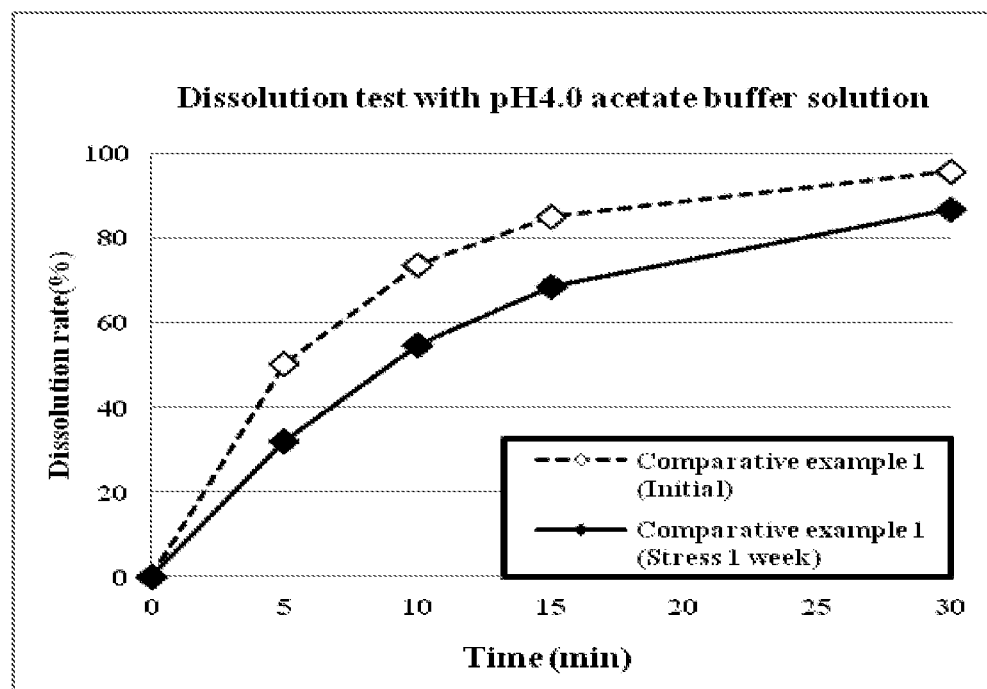

【Figure 4】
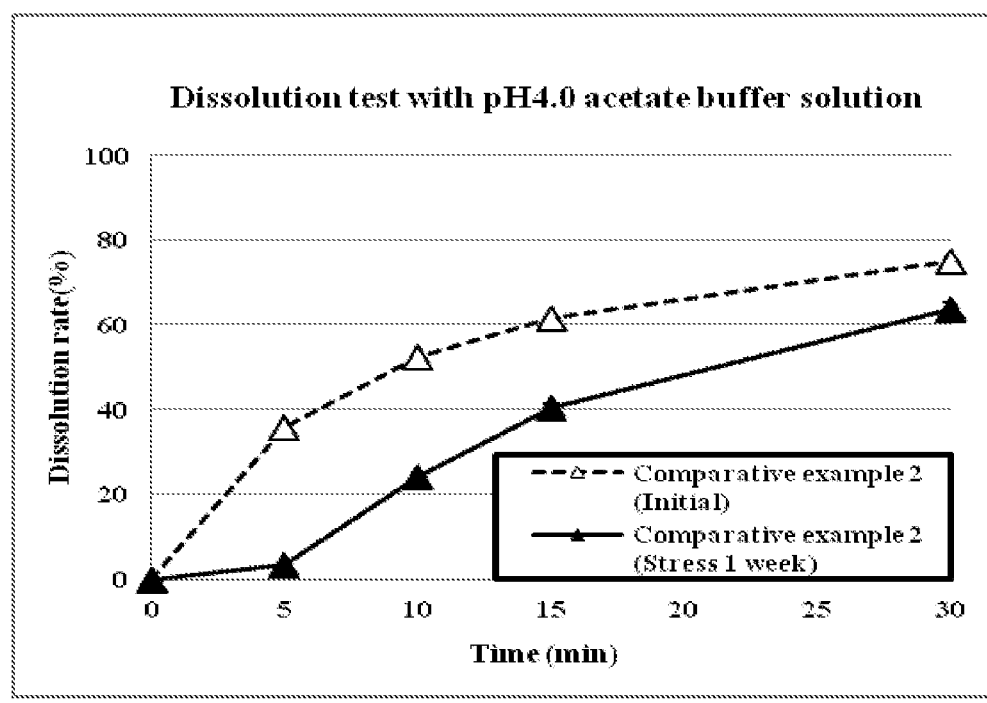

PREPARATION CONTAINING BENZIMIDAZOLE DERIVATIVE

TECHNICAL FIELD

The present invention relates to a formulation for oral administration comprising a benzimidazole derivative or a pharmaceutically acceptable salt thereof; and at least one disintegrant selected from the group consisting of croscarmellose sodium, sodium starch glycolate and low-substituted hydroxypropylcellulose.

BACKGROUND ART

It is obviously known in the art that even formulations comprising the same active component may show a difference in pharmaceutically important properties such as the solubility, dissolution characteristics and bioavailability of the active component comprised in the formulations depending on an additional constitutional component comprised therein. Thus, in addition to a development of a novel compound, it is also very important to develop a constituent comprised in a formulation so as to maximize a pharmacological effect of the novel, developed compound.

Meanwhile, (S)-4((5,7-difluorochroman-4-yl)oxy)-N,N-2-trimethyl-1H-benzo[d]imidazole-6-carboxamide is known to have a use for preventing and treating diseases mediated by an acid pump antagonistic activity, such as gastrointestinal diseases, for example, a gastroesophageal disease, a gastroesophageal reflux disease (GERD), a peptic ulcer, a gastric ulcer, a duodenal ulcer, an NSAID-induced ulcer, gastritis, a *Helicobacter pylori* infection, dyspepsia, functional dyspepsia, Zollinger-Ellison syndrome, a nonerosive reflux disease (NERD), a visceral pain, purosis, nausea, esophagitis, dysphagia, salivation, an airway lesion or asthma (WO 2007/072146).

However, the above compound has a problem in that its bioavailability and onset of drug action may become instable due to a phenomenon of decline in dissolution rate with an elapsed time of storage, thus still requiring a more research on solving such problem.

PRIOR ART REFERENCES

[Patent Document]
(Patent Document 1) International Patent No. WO 2007/072146

DISCLOSURE

Technical Problem

The objective of the present invention is to provide a novel formulation comprising a benzimidazole derivative, which is protected from having a phenomenon of decline in dissolution rate and also has an excellent storage stability.

Technical Solution

In one aspect for solving the above problem, the present invention provides a formulation for oral administration comprising a compound of (S)-4((5,7-difluorochroman-4-yl)oxy)-N,N-2-trimethyl-1H-benzo[d]imidazole-6-carboxamide of the following Formula 1 or a pharmaceutically acceptable salt thereof; and at least one disintegrant selected from the group consisting of croscarmellose sodium, sodium starch glycolate and low-substituted hydroxypropylcellulose:

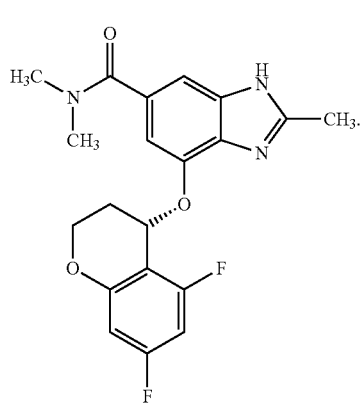

[Formula 1]

The above formulation for oral administration can be a tablet.

In the present invention, a compound of the above Formula 1 is a novel substance for preventing and treating gastrointestinal diseases and bleeding associated therewith by means of a pharmacological mechanism of a potassium competitive acid blocker (P-CAB). The compound of the above Formula 1 has difficulty in effectively exerting its drug action because the compound shows a serious phenomenon of decline in dissolution rate with an elapsed time of storage.

Accordingly, the present inventors have tried to prepare the compound of the above Formula 1 into various formulations, thus, to our surprise, finding that a formulation, which uses croscarmellose sodium, sodium starch glycolate or low-substituted hydroxypropylcellulose as a disintegrant, is protected from having a phenomenon of decline in dissolution rate and exhibits an excellent storage stability at the same time, such that the compound could be used as a formulation, of which dissolution is stable and storage stability is secured as well. More particularly, the inventive compound of Formula 1 can be combined with specific disintegrants of croscarmellose sodium, sodium starch glycolate or low-substituted hydroxypropylcellulose, such that a storage stability of the inventive compound can be secured just by means of a simple preparation process without an addition of a stabilizer constituent for securing the storage stability of drugs, or without a special preparation process or packing process. By doing so, the inventive compound can be unaffected by packing and storage conditions, and its dissolution can be stable and its storage stability can be secured at pH 4.0, which corresponds to a biological environment in stomach and intestines.

In the present invention, the above "(S)-4((5,7-difluorochroman-4-yl)oxy)-N,N-2-trimethyl-1H-benzo[d]imidazole-6-carboxamide," which is a type of benzimidazole derivative, exhibits an acid pump inhibitory activity.

In the present invention, a pharmaceutically acceptable salt of the compound of the above Formula 1 can be a pharmaceutically acceptable acid-addition salt.

Particularly, the above acid-addition salt can be selected from the group consisting of acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hybenzate, hydrochloride/chloride, hydrobromide/bromide, hydroiodide/iodide, isethionate, lactate, malate, maleate, malonate, mesylate, methylsulfate, naphthalate, 2-napsylate, nicotinate, nitrate, orotate, palmitate, pamoate, phosphate/hydrogen phosphate/dihydrogen phosphate, pyroglutamate, saccharate, stearate, succinate, tannate, tartrate, tosylate, trifluoroacetate and xinafoate salts, but is not limited thereto, and a salt, which may conventionally exhibit a pharmacological activity of the compound of the above Formula 1, can be used without a limitation.

A content of the compound of the above Formula 1 comprised in the inventive formulation as an active component or pharmaceutically acceptable salt thereof can be amount to 10 to 140 mg, particularly 20 to 120 mg, or 10 to 40 wt % with regard to the total weight of the formulation, but is not limited thereto, and can be a conventional one, at which the above compound or the pharmaceutically acceptable salt thereof can exhibit its pharmacological activity.

The formulation of the present invention comprises at least one disintegrant selected from the group consisting of croscarmellose sodium, sodium starch glycolate and low-substituted hydroxypropylcellulose.

In the present invention, the above low-substituted hydroxypropylcellulose is formed as a low-substituted hydroxypropyl ether of cellulose, a substitution degree of hydropropoxy group can amount to 5 to 16 mass %.

In one embodiment of the present invention, as a result of identifying a storage stability of a formulation, which was prepared by using croscarmellose sodium, sodium starch glycolate or low-substituted hydroxypropylcellulose as a disintegrant, it could be seen that the formulation was excellent in its storage stability because the formulation produced almost no impurities even after being stored for 7 days under a stress condition (60° C., 80% RH) (Tables 7 and 8).

Also, in one embodiment of the present invention, as a result of identifying a dissolution rate of a formulation, which was prepared by using croscarmellose sodium, sodium starch glycolate or low-substituted hydroxypropylcellulose as a disintegrant, it could be seen that the formulation was stable in its dissolution because the formulation exhibited almost no phenomenon of decline in dissolution rate under a condition similar to a biological environment in stomach and intestines, unlike a formulation, which was prepared by using crospovidone or Starch 1500 as a disintegrant (Tables 9 to 11 and FIGS. 1 to 4).

In the present invention, a content of the above disintegrant can be amount to 1 to 20 wt % with regard to the total weight of the formulation. If the content of the above disintegrant is comprised by less than 1 wt % with regard to the total weight of the formulation, a desired bioavailability rate cannot be obtained due to an excessive delay in disintegration, and if being comprised by more than 20 wt %, a property of the formulation and a quality conformance thereof cannot be secured due to its swelling phenomenon caused by a wetting property of the disintegrant.

The formulation according to the present invention can further comprise at least one selected from the group comprising a binder, a filler and a lubricant.

In the present invention, the term "binder" and "excipient" can be used interchangeably.

The formulation of the present invention comprises a binder, particularly wherein the binder can be at least one selected from the group comprising starch, microcrystalline cellulose, colloidal silicon dioxide, mannitol, lactose, polyethylene glycol, polyvinylpyrrolidone co-polymer, hydroxypropylcellulose, gelatin and a mixture thereof, and more particularly wherein it can be at least one selected from hydroxypropylcellulose, polyvinylpyrrolidone and copovidone.

A content of the above binder can be within a range of 1 to 40 wt % with regard to the total weight of the formulation. If the content of the above binder amounts to less than 1 wt %, it is difficult to prepare a granule having a desired hardness and size due to a lack of agglutination of the formulation. If the content amounts to more than 40 wt %, a desired bioavailability cannot be obtained due to an excessive delay in disintegration.

The formulation of the present invention comprises a filler, particularly wherein the filler can be at least one selected from the group comprising lactose, microcrystalline cellulose, mannitol and colloidal silicon dioxide, and more particularly wherein it can be one selected from the group comprising mannitol, microcrystalline cellulose and lactose, but is not limited thereto, and may be one conventionally used in the art.

A content of the above filler can be one conventionally used in the art, particularly wherein it can be properly chosen within a range of 1 to 99 wt % with regard to the total weight of the formulation.

The formulation of the present invention comprises a lubricant, particularly wherein the lubricant can be at least one selected from the group comprising stearic acid, magnesium stearate, calcium stearate, sodium benzoate, sodium stearyl fumarate, glyceryl monooleate, glyceryl monostearate, glyceryl behenate, glyceryl palmitostearate, zinc stearate and paraffin group, and more particularly wherein it can be magnesium stearate, but is not limited thereto and may be one conventionally used in the art.

A content of the above lubricant can be one conventionally used in the art, particularly wherein it can be properly chosen within a range of 0.5 to 10 wt % with regard to the total weight of the formulation.

The formulation of the present invention can be coated with a film coating agent, wherein the coating agent can be constituted by 0.5 to 10 wt % with regard to the total weight of the formulation.

The present invention provides a method for preparing a formulation comprising the compound of the above Formula 1. The formulation can be prepared by means of a known standard technology or a preparation method conventionally used in the art.

Particularly, the method for preparing the inventive formulation can comprise: (a) containing a compound of the above Formula 1 as an active component, combining a disintegrant, at least one diluent and other excipient therewith together, and granulating the resulting mixture by means of a binder solution containing a binder; and (b) drying the above obtained granular substance, adding an excipient, a disintegrant and a lubricant to the mixture substance and mixing them together, and compressing the resulting mixture as a tablet.

However, it is not limited to the above preparation method and can be subject to change according to a principle known in the art.

The present invention provides a pharmaceutical composition comprising a formulation with the compound of the above Formula 1 and the disintegrant.

The present invention provides a pharmaceutical composition for preventing or treating gastrointestinal diseases, comprising a formulation with the compound of the above Formula 1 and the disintegrant.

The formulation or the pharmaceutical composition of the present invention can comprise the compound of the above Formula 1, thus being used to prevent or treat gastrointestinal diseases mediated by an acid pump antagonistic activity.

In other aspect for solving the above problem, the present invention provides the use of a formulation comprising a compound of (S)-4((5,7-difluorochroman-4-yl)oxy)-N,N-2-trimethyl-1H-benzo[d]imidazole-6-carboxamide of Formula 1 or a pharmaceutically acceptable salt thereof; and at least one disintegrant selected from the group consisting of croscarmellose sodium, sodium starch glycolate and low-substituted hydroxypropylcellulose for oral administration.

In other aspect for solving the above problem, the present invention provides the use of a formulation comprising a compound of (S)-4((5,7-difluorochroman-4-yl)oxy)-N,N-2-trimethyl-1H-benzo[d]imidazole-6-carboxamide of Formula 1 or a pharmaceutically acceptable salt thereof; and at least one disintegrant selected from the group consisting of croscarmellose sodium, sodium starch glycolate and low-substituted hydroxypropylcellulose for manufacture of a medicament for oral administration.

Advantageous Effects

A formulation comprising a compound of Formula 1 according to the present invention or a pharmaceutically acceptable salt thereof; and at least one disintegrant selected from the group consisting of croscarmellose sodium, sodium starch glycolate, and low-substituted hydroxypropylcellulose, exhibits an excellent storage stability and has an effect on preventing a phenomenon of decline in dissolution rate, thus being usefully used as a formulation for oral administration.

DESCRIPTION OF DRAWINGS

FIG. 1 illustrates a graph of comparing dissolution rates of a tablet according to Example 1 with each other, respectively under initial and stress conditions, wherein the Example 1 comprises croscarmellose sodium.

FIG. 2 illustrates a graph of comparing dissolution rates of a tablet according to Example 12 with each other, respectively under initial and stress conditions, wherein the Example 12 comprises low-substituted hydroxypropylcellulose.

FIG. 3 illustrates a graph of comparing dissolution rates of a tablet according to Comparative Example 1 with each other, respectively under initial and stress conditions, wherein the Comparative Example 1 comprises crospovidone.

FIG. 4 illustrates a graph of comparing dissolution rates of a tablet according to Comparative Example 2 with each other, respectively under initial and stress conditions, wherein the Comparative Example 2 comprises Starch 1500.

MODE FOR INVENTION

Hereinafter, configuration and effects of the present invention will be described in more detail through preparation examples, examples and experimental examples. However, the following preparation examples, examples and experimental examples are provided only for the purpose of illustrating the present invention, and thus the present invention is not limited thereto.

Preparation Example 1: Preparing of a Tablet Containing Croscarmellose Sodium

A method for preparing a tablet of Example 1 is as follows.

A main active ingredient (S)-4((5,7-difluorochroman-4-yl)oxy)-N,N-2-trimethyl-1H-benzo[d]imidazole-6-carboxamide was mixed with mannitol, microcrystalline cellulose and croscarmellose sodium. Then, a binder solution comprising hydroxypropylcellulose and distilled water was added to a mixture resulting from the above mixing process, then a kneading and drying process, and then an sizing was carried out. After that, a substance resulting from the above sizing process was mixed with colloidal silicon dioxide and magnesium stearate, after which a resulting mixture was compressed into and prepared as a tablet. Contents of components comprised in the tablet of the above Example 1 are such as those shown in the following Table 1.

Tablets of Examples 2 and 3 were prepared by respectively using lactose and starch instead of mannitol, in comparison with the tablet of Example 1, but, except for that, they were prepared by means of the same method for preparing a tablet as described in the above Example 1. Contents of components comprised in the tablets of the above Examples 2 and 3 are such as those shown in the following Table 1.

Tablets of Examples 4 and 5 were prepared by respectively using polyvinylpyrrolidone and copovidone instead of hydroxypropylcellulose, in comparison with the tablet of Example 1, but, except for that, they were prepared by means of the same method for preparing a tablet as described in the above Example 1. Contents of components comprised in the tablets of the above Examples 4 and 5 are such as those shown in the following Table 1.

Tablets of Examples 6 to 9 were prepared by varying an amount of croscarmellose sodium, in comparison with the tablet of Example 1, but, except for that, they were prepared by means of the same method for preparing a tablet as described in the above Example 1. Contents of components comprised in the tablets of the above Examples 6 to 9 are such as those shown in the following Table 1.

A tablet of Example 10 was prepared by doubling an amount of a main active ingredient, in comparison with the tablet of Example 1, but, except for that, they were prepared by means of the same method for preparing a tablet as described in the above Example 1. Contents of components contained in the tablet of the above Example 10 are such as those shown in the following Table 1.

TABLE 1

| | | Example (Amount Used, mg) | | | | | | | | | |
|---|---|---|---|---|---|---|---|---|---|---|---|
| Classification | Component | 1 | 2 | 3 | 4 | 5 | 6 | 7 | 8 | 9 | 10 |
| Main active ingredient | (S)-4((5,7-difluorochroman-4-yl)oxy)-N,N-2-trimethyl-1H-benzo[d]imidazole-6-carboxamide | 50 | 50 | 50 | 50 | 50 | 50 | 50 | 50 | 50 | 100 |

TABLE 1-continued

| Classification | Component | Example (Amount Used, mg) | | | | | | | | | |
|---|---|---|---|---|---|---|---|---|---|---|---|
| | | 1 | 2 | 3 | 4 | 5 | 6 | 7 | 8 | 9 | 10 |
| Excipient | Mannitol | 50 | — | — | 50 | 50 | 54 | 44 | 40 | 30 | 100 |
| | Lactose | — | 62 | — | — | — | — | — | — | — | — |
| | Starch | — | — | 62 | — | — | — | — | — | — | — |
| | Microcrystalline cellulose | 80 | 68 | 68 | 80 | 80 | 80 | 80 | 80 | 80 | 160 |
| | Colloidal silicon dioxide | 2 | 2 | 2 | 2 | 2 | 2 | 2 | 2 | 2 | 4 |
| Disintegrant | Croscarmellose sodium | 10 | 10 | 10 | 10 | 10 | 6 | 16 | 20 | 30 | 20 |
| Binder | Hydroxypropylcellulose | 6 | 6 | 6 | — | — | 6 | 6 | 6 | 6 | 12 |
| | Polyvinylpyrrolidone | — | — | — | 6 | — | — | — | — | — | — |
| | Copovidone | — | — | — | — | 6 | — | — | — | — | — |
| Lubricant | Magnesium stearate | 2 | 2 | 2 | 2 | 2 | 2 | 2 | 2 | 2 | 4 |
| | Total Weight | 200 | 200 | 200 | 200 | 200 | 200 | 200 | 200 | 200 | 400 |

Preparation Example 2: Preparing of a Tablet Containing Sodium Starch Glycolate

Tablets of Examples 11 and 12 were prepared by using sodium starch glycolate instead of croscarmellose sodium as a disintegrant in comparison with the tablet of Example 1, but, except for that, they were prepared by means of the same method for preparing a tablet as described in the above Example 1. Contents of components comprised in the tablets of the above Examples 11 and 12 are such as those shown in the following Table 2.

TABLE 2

| Classification | Component | Example (Amount Used, mg) | |
|---|---|---|---|
| | | 11 | 12 |
| Main active ingredient | (S)-4((5,7-difluorochroman-4-yl)oxy)-N,N-2-trimethyl-1H-benzo[d]imidazole-6-carboxamide | 50 | 50 |
| Excipient | Mannitol | 50 | 62 |
| | Microcrystalline cellulose | 80 | 58 |
| | Colloidal silicon dioxide | 2 | 2 |
| Disintegrant | Sodium starch glycolate | 10 | 20 |
| Binder | Hydroxypropylcellulose | 6 | 6 |
| Lubricant | Magnesium stearate | 2 | 2 |
| | Total Weight | 200 | 200 |

Preparation Example 3: Preparing of a Tablet Containing Low-Substituted Hydroxypropylcellulose A tablet of Example 13 was prepared by using low-substituted hydroxypropylcellulose instead of croscarmellose sodium as a disintegrant in comparison with the tablet of Example 1, but, except for that, they were prepared by means of the same method for preparing a tablet as described in the above Example 1. Contents of components comprised in the tablet of the above Example 13 are such as those shown in the following Table 3.

TABLE 3

| Classification | Component | Example 13 (Amount Used, mg) |
|---|---|---|
| Main active ingredient | (S)-4((5,7-difluorochroman-4-yl)oxy)-N,N-2-trimethyl-1H-benzo[d]imidazole-6-carboxamide | 50 |
| Excipient | Mannitol | 50 |
| | Microcrystalline cellulose | 80 |
| | Colloidal silicon dioxide | 2 |
| Disintegrant | Low-substituted hydroxypropylcellulose | 10 |
| Binder | Hydroxypropylcellulose | 6 |
| Lubricant | Magnesium stearate | 2 |
| | Total Weight | 200 |

Preparation Example 4: Preparing of a Simple Mix Tablet Containing Sodium Starch Glycolate An excipient and a disintegrant, including a main active ingredient, were simply mixed and sized, after which a lubricant was further mixed therewith and a resulting mixture was pressed into a tablet, such that the tablet for oral administration of Example 14 was prepared. Contents of components comprised in the tablet of the above Example 14 are such as those shown in the following Table 4.

TABLE 4

| Classification | Component | Example 14 (Amount Used, mg) |
|---|---|---|
| Main active ingredient | (S)-4-((5,7-difluorochroman-4-yl)oxy)-N,N-2-trimethyl-1H-benzo[d]imidazole-6-carboxamide | 50 |
| Excipient | Lactose | 84 |
| | Silicified microcrystalline cellulose | 56 |
| | Colloidal silicon dioxide | 2 |
| Disintegrant | Sodium starch glycolate | 6 |
| Lubricant | Magnesium stearate | 2 |
| | Total Weight | 200 |

Preparation Example 5: Preparing of a Tablet Containing Crospovidone

A tablet for oral administration of Comparative Example 1, which used crospovidone as a disintegrant, was prepared by means of the same method for preparing a tablet as described in Example 1, with contents of components shown in the following Table 5.

TABLE 5

| Classification | Component | Comparative Example 1 (Amount Used, mg) |
|---|---|---|
| Main active ingredient | (S)-4((5,7-difluorochroman-4-yl)oxy)-N,N-2-trimethyl-1H-benzo[d]imidazole-6-carboxamide | 50 |
| Excipient | Mannitol | 62 |
|  | Microcrystalline cellulose | 68 |
|  | Colloidal silicon dioxide | 2 |

TABLE 5-continued

| Classification | Component | Comparative Example 1 (Amount Used, mg) |
|---|---|---|
| Binder | Hydroxypropylcellulose | 6 |
| Disintegrant | Crospovidone | 10 |
| Lubricant | Magnesium stearate | 2 |
|  | Total Weight | 200 |

Preparation Example 6: Preparing of a Tablet Containing Starch 1500

A tablet for oral administration of Comparative Example 2, which used Starch 1500 as a disintegrant, was prepared by means of the same method for preparing a tablet as described in Example 1, with contents of components shown in the following Table 6.

TABLE 6

| Classification | Component | Comparative Example 1 (Amount Used, mg) |
|---|---|---|
| Main active ingredient | (S)-4((5,7-difluorochroman-4-yl)oxy)-N,N-2-trimethyl-1H-benzo[d]imidazole-6-carboxamide | 50 |
| Excipient | Mannitol | 50 |
|  | Microcrystalline cellulose | 80 |
|  | Colloidal silicon dioxide | 2 |
| Binder | Hydroxypropylcellulose | 6 |
| Disintegrant | Starch 1500 | 10 |
| Lubricant | Magnesium stearate | 2 |
|  | Total Weight | 200 |

Experimental Example 1: Storage Stability Test

Tablets of Examples 1 to 14, prepared according to the above Preparation Examples 1 to 4, were inserted into each of high-density polyethylene (HDPE) bottles, after which resulting bottles were stored under a stress condition (60° C., 80% RH) for 7 days, such that properties of the tablets were identified and a purity test thereof was carried out as well.

(1) Impurity Test Evaluation on Tablet Comprising Croscarmellose Sodium

Particularly, as a result of carrying out an evaluation on the occurrence or increase of impurities after the storage of the tablets of Examples 1 to 10, as prepared by using croscarmellose sodium as a disintegrant, no pattern of occurrence or increase of impurities was identified in all the tablets of Examples 1 to 10 (Table 7).

TABLE 7

|  |  | Example |  |  |  |  |  |  |
|---|---|---|---|---|---|---|---|---|
| Component (%) |  | 1 | 2 | 3 | 4 | 5 | 9 | 10 |
| Initial Condition | Content (API) | 99.94 | 99.94 | 99.81 | 99.94 | 99.79 | 99.93 | 100.00 |
|  | Total impurities | 0.06 | 0.06 | 0.19 | 0.06 | 0.21 | 0.07 | 0.00 |
| Stress Condition Storage for 7 Days | Content (API) | 99.94 | 99.94 | 99.80 | 99.94 | 99.81 | 99.93 | 99.98 |
|  | Total impurities | 0.06 | 0.06 | 0.2 | 0.06 | 0.19 | 0.07 | 0.02 |

Accordingly, the formulation comprising the compound of Formula 1, which used croscarmellose sodium as a disintegrant, produced almost no impurities, thus identifying that the formulation was excellent in storage stability.

(2) Purity Test Evaluation on Tablet Comprising Sodium Starch Glycolate or Low-Substituted Hydroxypropylcellulose Particularly, as a result of carrying out an evaluation on a production or increase of impurities after the storage of the tablets of Examples 11 to 12, as prepared by using sodium starch glycolate as a disintegrant, as well as the tablet of Example 13, as prepared by using low-substituted hydroxypropylcellulose as a disintegrant, it was identified that no pattern of occurrence or increase of impurities was identified in all the tablets of the Examples 11 to 13 (Table 8).

TABLE 8

|  |  | Example |  |
|---|---|---|---|
| Component (%) |  | 11 | 13 |
| Initial Condition | Content (API) | 99.84 | 99.94 |
|  | Total impurities | 0.16 | 0.06 |
| Stress Condition Storage for 7 Days | Content (API) | 99.83 | 99.93 |
|  | Total impurities | 0.17 | 0.07 |

Accordingly, a formulation comprising the compound of Formula 1, which used sodium starch glycolate or low-substituted hydroxypropylcellulose as a disintegrant, produced almost no impurities, thus identifying that the formulation was excellent in storage stability.

Experimental Example 2: Dissolution Stability Test

Tablets of Examples 1 to 14, prepared according to the above Preparation Examples 1 to 4, were inserted into each of high-density polyethylene (HDPE) bottles, after which resulting bottles were stored under a stress condition (60° C., 80% RH) for 7 days, such that an in vitro dissolution test and an HPLC analysis were carried out.

(1) Evaluation on Dissolution Rate of Tablet Comprising Croscarmellose Sodium

Particularly, a dissolution experiment was carried out on tablets of Examples 1 to 10, as prepared by using croscarmellose sodium as a disintegrant, wherein conditions for the dissolution experiment were such as those described below:

1) Basis of dissolution test: Dissolution test method in general test methods in the 11$^{th}$ Revision of the Korean Pharmacopoeia
2) Dissolution test method: Dissolution test method II, paddle method
3) Dissolution test solution: 900 ml of pH 4.0 acetate buffer solution
4) Temperature condition: Maintained at 37.2° C.±0.5° C.
5) Analysis method: HPLC method
  Detector: Ultraviolet absorptiometer (measurement wavelength: 262 nm)
  Column: C18 5 um/4.6×150 mm column
  Mobile phase: Acetonitrile: Distilled water [gradient]

As a result of comparing dissolution rates with each other at a time of 15 minutes after onset of dissolution, it was found that the dissolution rates fall within the specified criteria, and it was identified that there occurred no phenomenon of decline in dissolution rate in all the tablets of the Examples 1 to 10 (Table 9 and FIG. 1).

TABLE 9

| Time | Example | | | | | | | | | |
|---|---|---|---|---|---|---|---|---|---|---|
| (15 Minutes) | 1 | 2 | 3 | 4 | 5 | 6 | 7 | 8 | 9 | 10 |
| Dissolution Rate (%) under Initial Condition | 85.0 | 80.6 | 80.7 | 86.5 | 81.5 | 85.0 | 88.8 | 86.0 | 81.9 | 77.1 |
| Dissolution Rate (%) under Stress Condition (7 days in storage) | 85.7 | 78.1 | 75.5 | 84.0 | 85.1 | 81.3 | 89.4 | 84.2 | 82.0 | 76.6 |

(2) Evaluation on Dissolution Rate of Tablet Comprising Sodium Starch Glycolate or Low-Substituted Hydroxypropylcellulose Particularly, a dissolution experiment was carried out on tablets of Examples 11, 12 and 14, as prepared by using sodium starch glycolate as a disintegrant, as well as a tablet of Example 13, as prepared by using low-substituted hydroxypropylcellulose as a disintegrant, wherein conditions for the dissolution experiment were such as those described below:
1) Basis of dissolution test: Dissolution test method in general test methods in the 11$^{th}$ Revision of the Korean Pharmacopoeia
2) Dissolution test method: Dissolution test method II, paddle method
3) Dissolution test solution: 900 ml of pH 4.0 acetate buffer solution
4) Temperature condition: Maintained at 37.2° C.±0.5° C.
5) Analysis method: HPLC method
  Detector: Ultraviolet absorptiometer (measurement wavelength: 262 nm)
  Column: C18 5 um/4.6×150 mm column
  Mobile phase: Acetonitrile: Distilled water [gradient]

As a result of comparing dissolution rates with each other at a time of 15 minutes after onset of dissolution, it was found that the dissolution rates fall within the specified criteria, it was identified that there occurred no phenomenon of decline in dissolution rate in all the tablets of the Examples 11 to 14 (Table 10 and FIG. 2).

TABLE 10

| | Example | | | |
|---|---|---|---|---|
| Time (15 Minutes) | 11 | 12 | 13 | 14 |
| Dissolution Rate (%) under Initial Condition | 85.5 | 84.8 | 76.8 | 81.1 |
| Dissolution Rate (%) under Stress Condition (7 days in storage) | 82.3 | 84.7 | 75.3 | 79.6 |

(3) Evaluation on Dissolution Rate of Tablet Comprising Crospovidone or Starch 1500

Particularly, a dissolution experiment was carried out on tablets of Comparative Examples 1 and 2, as prepared by using crospovidone or Starch 1500 as a disintegrant, wherein conditions for the dissolution experiment were such as those described below:
1) Basis of dissolution test: Dissolution test method out of general test methods in the 11$^{th}$ Revision of the Korean Pharmacopoeia
2) Dissolution test method: Dissolution test method II, paddle method
3) Dissolution test solution: 900 ml of pH 4.0 acetate buffer solution
4) Temperature condition: Maintained at 37.2° C.±0.5° C.
5) Analysis method: HPLC method
  Detector: Ultraviolet absorptiometer (measurement wavelength: 262 nm)
  Column: C18 5 um/4.6×150 mm column
  Mobile phase: Acetonitrile: Distilled water [gradient]

As a result of comparing dissolution rates with each other at a time of 15 minutes after onset of dissolution, it was identified that there occurred a phenomenon of decline in dissolution rate after storage in the stress condition in comparison with the initial condition (Table 11 and FIGS. 3 and 4).

TABLE 11

| | Comparative Example | |
|---|---|---|
| Time (15 Minutes) | 1 | 2 |
| Dissolution Rate (%) under Initial Condition | 85.2 | 61.7 |
| Dissolution Rate (%) under Stress Condition (7 days in storage) | 68.6 | 40.3 |

According to the Experimental Example 2 above, it was identified that the formulation, as prepared by using croscarmellose sodium, sodium starch glycolate or low-substituted hydroxypropylcellulose as a disintegrant, showed almost no phenomenon of decline in dissolution rate at pH 4.0, which is a biological environment in stomach and intestines, when compared to the formulation, as prepared by using crospovidone or Starch 1500 as a disintegrant.

While certain portions of the present invention have been described in detail above, such specific descriptions are set forth only to illustrate preferred exemplary embodiments, so it is obvious to those skilled in the art that the scope of the present invention is not limited thereto.

Therefore, the actual scope of the present invention will be defined by the accompanying claims and equivalents thereto.

The invention claimed is:

1. A formulation for oral administration comprising a compound of (S)-4((5,7-difluorochroman-4-yl)oxy)-N,N-2-trimethyl-1H-benzo[d]imidazole-6-carboxamide of Formula 1 or a pharmaceutically acceptable salt thereof; and at least one disintegrant selected from the group consisting of croscarmellose sodium, sodium starch glycolate and low-substituted hydroxypropylcellulose, wherein the formulation is a tablet; and wherein a dissolution rate of the tablet increases or decreases by less than 6% from an initial value when stored under a stress condition of 60° C. and 80% relative humidity for 7 days:

[Formula 1]

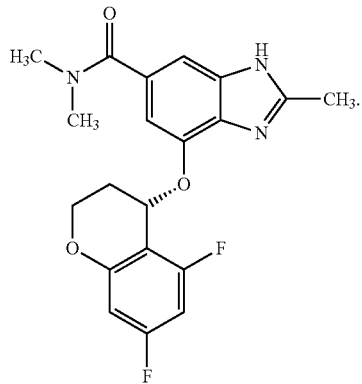

2. The formulation for oral administration according to claim 1, wherein a content of the disintegrant is 1 to 20 wt % of the total weight of the formulation.

3. The formulation for oral administration according to claim 1, wherein the disintegrant is low-substituted hydroxypropylcellulose having a substitution degree of a hydroxypropoxy group that amounts to 5 to 16 mass %.

4. The formulation for oral administration according to claim 1, wherein the formulation further comprises at least one ingredient selected from the group consisting of a binder, a filler and a lubricant.

5. The formulation for oral administration according to claim 4, wherein the binder is at least one selected from the group consisting of starch, microcrystalline cellulose, colloidal silicon dioxide, mannitol, lactose, polyethylene glycol, polyvinyl pyrrolidone co-polymer, hydroxypropyl cellulose, gelatin and a mixture thereof.

6. The formulation for oral administration according to claim 4, wherein the filler is at least one selected from the group consisting of lactose, microcrystalline cellulose, mannitol and colloidal silicon dioxide.

7. The formulation for oral administration according to claim 4, wherein the lubricant is at least one selected from the group consisting of stearic acid, magnesium stearate, calcium stearate, sodium benzoate, sodium stearyl fumarate, glyceryl monooleate, glyceryl monostearate, glyceryl behenate, glyceryl palmitostearate, zinc stearate and a paraffin group.

* * * * *